United States Patent [19]

Ooi et al.

[11] Patent Number: 4,956,062
[45] Date of Patent: Sep. 11, 1990

[54] METHOD FOR CONCENTRATION DETERMINATION OF LITHIUM IONS

[75] Inventors: Kenta Ooi, Kagawa; Yoshitaka Miyai, Takamatsu; Shunsaku Katoh, Kagawa, all of Japan

[73] Assignee: Japan as represented by Director General of Agency of Industrial Science and Technology, Tokyo, Japan

[21] Appl. No.: 324,040

[22] Filed: Mar. 14, 1989

[30] Foreign Application Priority Data

Apr. 14, 1988 [JP] Japan ................................... 63-92600

[51] Int. Cl.$^5$ .......................................... G01N 27/333
[52] U.S. Cl. ................................. 204/153.15; 204/419
[58] Field of Search ....................... 204/1 A, 416–419

[56] References Cited

U.S. PATENT DOCUMENTS

| | | | |
|---|---|---|---|
| 3,809,638 | 5/1974 | Higashiyama et al. | 204/419 |
| 3,909,384 | 9/1975 | Sasinski et al. | 204/419 |
| 4,504,368 | 3/1985 | Delton et al. | 204/1 A |
| 4,613,422 | 9/1986 | Lauks | 204/416 |
| 4,665,049 | 5/1987 | Miyai et al. | 502/400 |
| 4,770,759 | 9/1988 | Young et al. | 204/418 |

FOREIGN PATENT DOCUMENTS

| | | | |
|---|---|---|---|
| 0168151 | 12/1981 | Japan | 204/419 |
| 965663 | 8/1964 | United Kingdom | 204/1 A |

Primary Examiner—T. Tung
Attorney, Agent, or Firm—Wenderoth, Lind & Ponack

[57] ABSTRACT

A highly sensitive and reliable electrochemical method is proposed for the determination of the lithium ion concentration in an aqueous medium, e.g., blood of a patient suffering depression and administrated with a lithium-containing medicament, by measuring the electromotive force between the medium and a powdery non-selective electrode, which is a non-stoichiometric composite oxide of lithium and manganese of the formula $Li_xMn_2O_4$, x being a positive number smaller than 1, prepared by partially leaching lithium ions out of a spinel-type lithium manganate $LiMn_2O_4$ with an acid, dipped in the medium. The ion-selective electrode can be in the form of a thin film or coating layer on an electrode element. This film or layer can be formed of a polymeric resin as a binder for the powdery composite oxide.

6 Claims, 2 Drawing Sheets

METHOD FOR CONCENTRATION DETERMINATION OF LITHIUM IONS

BACKGROUND OF THE INVENTION

The present invention relates to a method for the determination of the concentration of lithium ions in an aqueous medium. More particularly, the invention relates to an electrochemical method of high sensitivity and reliability for the determination of the concentration of lithium ions in an aqueous medium which also contains ions of other alkali metals and alkaline earth metals even when the concentration of lithium ions is very low.

As is known, lithium compounds are widely used, among many other important applications, as a therapeutic medicament for psychopathic patients suffering depression. It is important in the therapeutic treatment of a patient of depression by administration of a lithium containing medicament that the concentration of lithium ions in the blood is maintained at an effective level, for example, in the range from 0.5 to 1.0 mM. When the concentration of lithium ions in blood is too low, the therapeutic effect obtained thereby is of course insufficient. When the concentration of lithium ions in blood is too high, for example, in the range from 2.0 to 2.5 mM, on the other hand, various side effects are caused. Therefore, it is essential to periodically monitor the lithium ion concentration in the patient's blood and it is eagerly desired in the psychopathology to develop an accurate, rapid and convenient method for the determination of lithium ions in blood.

No practical method or apparatus, which meets the above mentioned requirements, however, is known mainly because blood always contains ions of alkali metals other than lithium, i.e., sodium and potassium, and alkaline earth metals, e.g., typically, calcium, in concentrations much higher than the lithium ion concentration to interfere detection and determination of lithium ions.

Several electrochemical methods have been proposed by using a sensor membrane electrode containing a neutral lithium ionophore. Examples of such an ionophore include crown ethers such as 14 crown-4-derivatives and 15-crown-4-derivatives disclosed in Journal of the American Chemical Society, Volume 106 (1984), page 6978, amide ethers disclosed in Analytical Chemistry, volume 58 (1986), page 1948, polypropoxylate adducts disclosed in Analyst, Volume 110 (1985), page 1381 and the like. A comprehensive review is given for lithium ion selective electrodes in ion-Selective Electrode Review, Volume 8 (1986), page 173. Sensors, e.g., electrodes, using these lithium ionophores are influenced by sodium ions badly affecting the accuracy of the concentration determination of lithium ions in blood.

SUMMARY OF THE INVENTION

The present invention accordingly has an object to provide a novel and practical electrochemical method for the rapid, accurate and convenient determination of the lithium ion concentration in blood or other aqueous media by use of a unique lithium ion selective sensor even in the presence of ions of alkali metals other than lithium and alkaline earth metals in relatively high concentrations. The most characteristic feature of the inventive method consists in the use of a unique electrochemical sensor which is a composite oxide of manganese and lithium.

Thus, the method of the present invention for the determination of the concentration of lithium ions in an aqueous medium comprises the steps of:

(a) bringing a composite oxide of manganese and lithium having a chemical composition expressed by the formula $Li_xMn_2O_4$, in which the subscript x is a positive number smaller than 1, into contact with the aqueous medium containing lithium ions; and (b) measuring the electromotive force generated between the aqueous medium and the composite oxide of manganese and lithium by using an electrode element in contact with the composite oxide.

Conveniently, measurement of the electromotive force is undertaken with a metal-made measuring electrode element inserted into a layer of a fine powder of the composite oxide dispersed and settled in the lithium ion containing aqueous medium. Alternatively, the metal-made measuring electrode element dipped in the lithium ion containing aqueous medium is provided with a coating layer on an electrode element or a thin film containing a fine powder of the composite oxide dispersed therein.

It is important that the composite oxide of manganese and lithium has a crystalline structure of a spinel compound of the formula $LiMn_2O_4$, of which a substantial portion of the sites for lithium ions is vacant corresponding to the formula $Li_xMn_2O_4$, in which x is a positive integer smaller than 1.

DETAILED DESCRIPTION OF THE PREFERRED EMBODIMENTS

Figure 1:
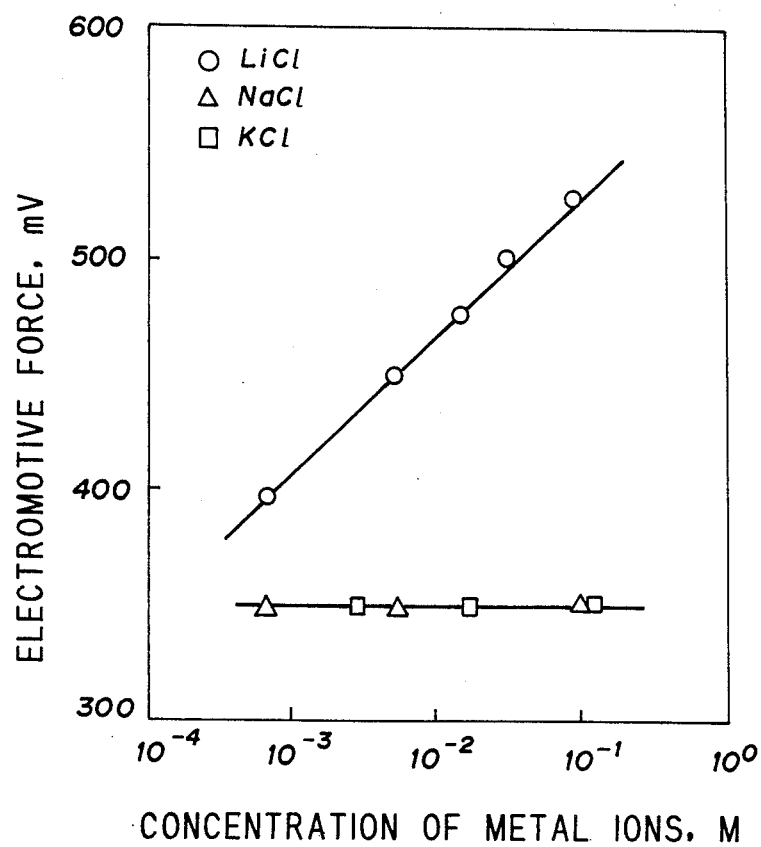
FIGS. 1 and 2 are each a graph showing the electromotive force generated on the lithium ion sensor used in the inventive method and on a $\beta$-manganese dioxide sensor, respectively, when the sensor is in an aqueous solution of lithium chloride, sodium chloride or potassium chloride as a function of the concentration of the metal ions of the respective salt.

The composite oxide of manganese and lithium used as the sensor in the inventive method is expressed by a chemical formula $Li_xMn_2O_4$, in which x is a positive integer smaller than 1. Methods for the preparation of such a composite oxide are described, for example, in Japanese Patent Kokai No. 61—283341, U.S. Pat. No. 4,665,049, Journal of Solid State Chemistry, Volume 39 (1981), page 142 and Journal of Solid State Chemistry, Volume 67 (1987), page 316. Namely, an oxide or a thermally decomposable compound of lithium and an oxide or a thermally decomposable compound of manganese each in a fine powdery form are intimately blended together and the powder blend is subjected to a heat treatment at a temperature of 200° C. or higher or, usually, in the range from 400° to 800° C. for at least 1 hour or, preferably, at least 3 hours in an oxidizing atmosphere to form a spinel-type compound or lithium manganate of the formula $LiMn_2O_4$ followed by leaching of a portion of the lithium ions out of the spinel compound with an acid. Examples of suitable oxides and thermally decomposable compounds of lithium and manganese include hydroxides i.e. LiOH, $Mn(OH)_2$ and MnO(OH), oxides, i.e., $Li_2O$, $MnO_2$ and $Mn_2O_3$, carbonates, i.e., $Li_2CO_3$ and $MnCO_3$, hydrogen carbonates, i.e. $LiHCO_3$, nitrates, i.e., $LiNO_3$ and $Mn(NO_3)_2$, halides, i.e., LiCl and LiBr and the like. Though not essential, the powders of the lithium compound and the manganese compound are blended in a proportion substantially equal to 1:2 relative to the respective metallic elements so that the resultant spinel compound can be free from other phases. Techniques of X-ray diffractometry are useful to confirm formation of the spinel compound $LiMn_2O_4$. The thus obtained spinel compound $LiMn_2O_4$ is then immersed in an aqueous acid solution to leach out a portion of the lithium ions therefrom. The acid is not particularly limitative provided no insoluble salt is formed between lithium ions and the acid. Examples of suitable acids include inorganic acids, e.g., hydrochloric, sulfuric, nitric and phosphoric acids, and organic acids, e.g., formic and acetic acid. Two kinds or more of these acids can be used as a mixture. The aqueous acid solution should have a pH not exceeding 6 or, preferably, not exceeding 3. The acid-leaching treatment is performed by dispersing the spinel compound in a fine powdery form in the aqueous acid solution and agitating the suspension for at least 1 hour or, in some cases, for several days, usually, at room temperature followed by collection of the powder, for example, by filtration, thorough washing with water and drying. Leaching of the lithium ions from the lithium manganate with an acid, e.g., hydrochloric acid, proceeds according to the following reaction equation:

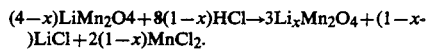

$(4-x)LiMn_2O_4 + 8(1-x)HCl \rightarrow 3Li_xMn_2O_4 + (1-x)LiCl + 2(1-x)MnCl_2.$ The leaching treatment of the lithium ions from the lithium manganate should be performed, preferably, to such an extent that the subscript x in the chemical formula $Li_xMn_2O_4$ expressing the lithium deficient spinel compound has a value in the range from 0.1 to 1.0 or, more preferably, from 0.6 to 0.96 corresponding to a molar ratio of Li:Mn in the range from 0.05 to 0.5 or, more preferably, from 0.3 to 0.48, especially, when the sensor is used for the determination of the lithium ion concentration in a weakly alkaline aqueous medium such as blood. When the extent of lithium ion leaching is limited as mentioned above, the spinel structure of the lithium manganate is retained as such as is disclosed in Journal of Solid State Chemistry, Volume 39 (1981), page 142. The values of x in the chemical formula can be determined by a method of chemical analysis.

The thus prepared composite oxide of lithium and manganese, i.e., lithium deficient spinel compound, in a powdery form can be used as such as an ion-selective electrode for lithium ions in an aqueous medium. Namely, the powder is dispersed and settled in a lithium ion-containing aqueous medium, e.g., blood, and a platinum electrode element inserted to the powder deposit on the vessel bottom serves as a conductor lead for the ion-selective electrode. The electromotive force between the ion-selective electrode and a reference electrode such as a saturated calomel electrode is measured according to a conventional electrochemical procedure. The powder should have a particle size distribution in the range from 0.5 to 5 μm. It is of course optional that the powder is shaped by compression into a shaped body to serve as a sensor member.

Alternatively, the powder of the composite oxide is blended with a polymeric material as a binder in such a proportion that the ratio of polymeric material:composite oxide is 30:70 by weight and the blend is shaped into a thin film having a thickness of from about 20 to about 200 μm to serve as a sensor member. Examples of suitable polymeric material include thermoplastic resins such as poly(vinyl chloride), acrylic resins and the like and rubbery elastomers such as silicone rubbers, various kinds of organic synthetic rubbers and the like. It is optional that such a blend is dissolved and dispersed in a suitable organic solvent to give a liquid coating composition with which a metal made, e.g., platinum-made, electrode element is coated by a suitable coating means followed by drying to give a coating layer of the blend which serves as the ion-selective electrode. The coating layer of such an ion-selective electrode should have a thickness in the range from 20 to 200 μm. When the thickness of the film or coating layer is too small, the ion-selective electrode would have only limited durability while, when the thickness thereof is too large, an undesirable decrease is caused in the sensitivity of the sensor.

When the lithium ion-selective electrode prepared in the above described manner and used in the inventive method is dipped in an aqueous medium containing lithium ions, selective adsorption of the lithium ions presumably takes place on the ion-selective electrode as a kind of so-called topochemical reaction to exhibit an electromotive force between the electrode and the aqueous medium and the electromotive force corresponds to the Nernst's gradient in a range of lithium ion concentration from 0.1 mM to 0.1 M. The electromotive force is not or little influenced by the coexisting ions of sodium, potassium, calcium and the like contained in the aqueous medium unless the concentration of these interfering ions in the medium exceeds 1 M. The electromotive force is also stable against changes in the pH of the aqueous medium although it is recommendable to conduct the measurement in a buffered aqueous medium or to make a correction of the measured electromotive force for the variation of the pH value when a very exact determination is desired. When the method of the invention is applied to the determination of the lithium ion concentration in an actual sample solution by using a film prepared as mentioned above as an ion-selective electrode membrane, an electrochemical cell is constructed which is expressed, for example, by the scheme of,

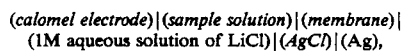

*(calomel electrode)|(sample solution)|(membrane)|*
(1M aqueous solution of LiCl)|*(AgCl)*|(Ag), though not particularly limitative thereto.

As is understood from the above given description, the method of the present invention provides an accurate, rapid, convenient and reliable means for the clinical determination of the lithium ion concentration in patient's blood because the electromotive force generated in the sensor is not or little influenced by the coexisting ions of sodium, potassium, calcium and the like along with the stability of the sensor in blood and absence of toxicity in the sensor material.

In the following, examples and comparative examples are given to illustrate the inventive method in more detail but not to limit the scope of the invention in any way.

EXAMPLE 1

A powder compact of a blend of 8.8 g of manganese(III) hydroxide MnO(OH) and 1.85 g of lithium carbonate $Li_2CO_3$ was subjected to a heat treatment in air at 800° C. for 4 hours. An X-ray diffractometric inspection of the thus obtained material indicated formation of lithium manganate LiMn$_2$O$_4$ having a crystalline structure of spinel. The lithium manganate was finely pulverized and immersed in 0.01 M hydrochloric acid at room temperature for 4 hours followed by filtration, washing with water and drying to give a powdery product having an average particle diameter of 1.2 μm. Results of a chemical analysis of this powdery product indicated that the powder was expressed by a chemical formula Li$_{0.66}$Mn$_2$O$_4$. The crystalline structure of spinel was retained after the above mentioned acid leaching treatment.

Each a 100 mg portion of the powder was dispersed and settled in 10 ml of an aqueous solution containing lithium chloride, sodium chloride or potassium chloride in different concentrations having a pH of 8.2 by using an ammonium chloride-ammonia buffer solution and measurements of the electromotive force were conducted at 25° C. between a platinum electrode inserted into the powder layer on the vessel bottom and a saturated calomel electrode as a reference immersed in the salt solution using a potentiometer. The results are shown in FIG. 1 for each salt as a function of the concentration of the salt in the solution.

As is clear from this figure, the electromotive force was independent of the ion concentration when the salt was sodium or potassium chloride while the electromotive force was increased linearly on the semi-logarithmic plot as the ion concentration was increased in the range from 10$^{-4}$ to 1 M when the salt was lithium chloride indicating the selective sensitivity of the ion sensor.

Separately from the above described measurements, the influences of coexisting ions of sodium, potassium and calcium were studied in the same measuring procedure of the electromotive force as above except that the aqueous solution of 0.01 M lithium chloride further contained 0.5 M of sodium chloride, 0.5 M of potassium chloride or 0.05 M of calcium chloride to give the electromotive forces of 470 mV, 462 mV and 470 mV, respectively, to be almost identical with the value of 464 mV in the absence of these interfering ions.

Comparative Example

Figure 2:
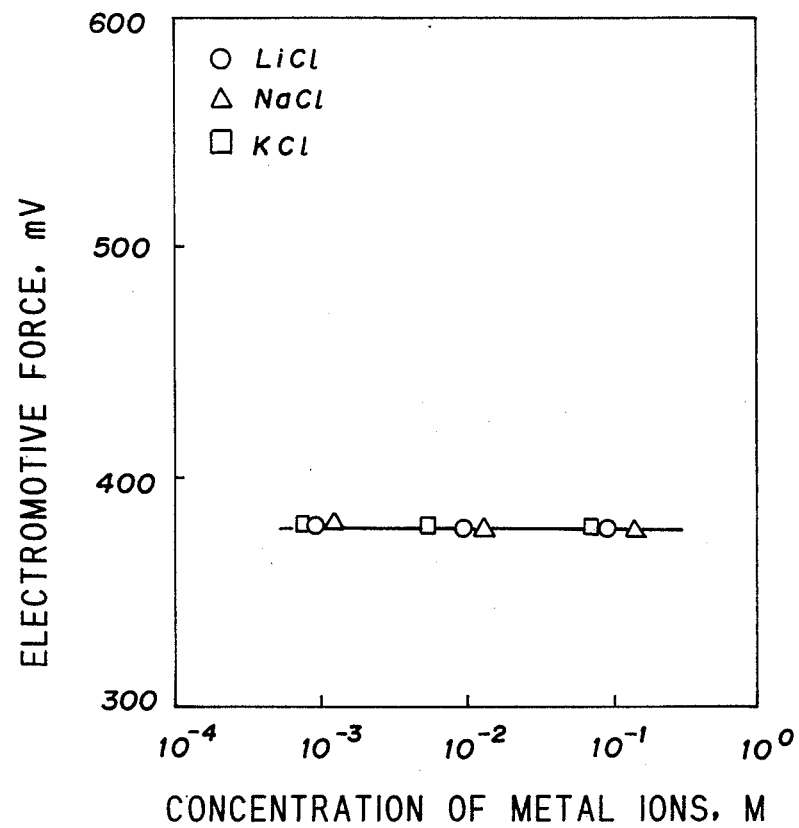

Measurements of electromotive force were conducted in just the same manner as in Example 1 excepting replacement of the powdery lithium deficient spinel compound with a powder of commercially available β-manganese dioxide having an approximately identical average particle diameter as above. The results are shown in FIG. 2 which clearly indicates that the electromotive force was identical for the three kinds of the salts and independent on the concentration of the salt in the aqueous solution.

EXAMPLE 2

A substantially identical procedure with Example 1 was undertaken for the preparation of powdery lithium deficient spinel compounds of the formula Li$_x$Mn$_2$O$_4$, in which the subscript x was 0.12 or 0.68, having an average particle diameter of 1.0 μm. Each a 1 g portion of the powders was added to 10 ml of a tetrahydrofuran solution containing 100 mg of a poly(vinyl chloride) resin dissolved therein. A platinum electrode element was coated with the thus prepared dispersion in the polymer solution as the coating composition followed by evaporation of the solvent to dryness to provide the platinum electrode element with a coating layer having a thickness of about 50 μm.

The thus prepared platinum electrode element with a sensor layer was dipped in 10 ml of an aqueous solution of lithium chloride in a varied concentration and the electromotive force thereof was measured at 25° C. in the same manner as in Example 1 with a saturated calomel electrode as the reference electrode. The results were as shown in Table 1 below.

TABLE 1

| Concentration of LiCl, M | Electromotive force, mV | |
|---|---|---|
| | x = 0.12 | x = 0.68 |
| 0.001 | 683 | 475 |
| 0.003 | 707 | 502 |
| 0.01 | 750 | 527 |
| 0.03 | 783 | 543 |

EXAMPLE 3

A 100 mg portion of the same powdery lithium-deficient spinel compound expressed by the formula Li$_{0.68}$Mn$_2$O$_4$ as used in Example 2 was dispersed in 10 ml of a tetrahydrofuran solution containing 100 mg of a poly(vinyl chloride) resin dissolved therein and the thus prepared liquid dispersion was cast on a glass plate followed by evaporation of the solvent to dryness. The polymeric film formed on the glass plate and peeled off the glass surface had a thickness of about 100 μm.

The above prepared polymeric film was used as an ion-selective membrane electrode to construct an electrochemical cell of the scheme:

(calomel electrode)|(sample solution)|(membrane)|
(1M aqueous solution of LiCl)|(AgCl)|(AgCl), with an aqueous solution of lithium chloride in a concentration varied in the range from 0.0001 to 0.01 M as the sample solution.

The results of the measurements of the electromotive force in this electrochemical cells were as shown in Table 2 below.

TABLE 2

| LiCl concentration in sample solution, M | Electromotive force, mV |
|---|---|
| 0.0001 | 153 |
| 0.0003 | 173 |
| 0.001 | 195 |
| 0.003 | 217 |
| 0.01 | 243 |

What is claimed is:

1. A method for the determination of the concentration of lithium ions in an aqueous medium, which consists essentially of the steps of:
   (a) bringing an ion-selective electrode comprising a composite oxide of manganese and lithium having a chemical composition expressed by the formula Li$_x$Mn$_2$O$_4$, in which the subscript x is a positive number smaller than 1, and a reference electrode into contact with the aqueous medium containing lithium ions; and
   (b) measuring the electromotive force generated between the reference electrode and the ion-selective electrode in said aqueous medium, said electromotive force being a function of said concentration of lithium ions.

2. The method for the determination of the concentration of lithium ions in an aqueous medium as claimed in claim 1 wherein the composite oxide of manganese and lithium is in the form of a powder.

3. The method for the determination of the concentration of lithium ions in an aqueous medium as claimed in claim 2 wherein the ion-selective electrode comprises a metal element inserted into a layer of the powder of the composite oxide settled in the lithium ion-containing aqueous medium.

4. The method for the determination of the concentration of lithium ions in an aqueous medium as claimed in claim 2 wherein the ion-selective electrode comprises a metal element provided with a coating layer comprising the powder of the composite oxide dispersed in a polymeric material.

5. The method for the determination of the concentration of lithium ions in an aqueous medium as claimed in claim 2 wherein the powder of the composite oxide has a particle diameter in the range from 0.5 $\mu$m to 5 $\mu$m.

6. The method for the determination of the concentration of lithium ions in an aqueous medium as claimed in claim 1 wherein the subscript $x$ has a value in the range from 0.1 to 1.0.

* * * * *